(12) United States Patent
Von Keudell et al.

(10) Patent No.: US 11,009,472 B2
(45) Date of Patent: May 18, 2021

(54) APPARATUS AND METHOD FOR SCANNING FOOD BARS WITH MOVABLE SCANNING UNIT

(71) Applicant: WEBER MASCHINENBAU GMBH BREIDENBACH, Breidenbach (DE)

(72) Inventors: Leopold Von Keudell, Salem (DE); Tobias Weber, Biedenkopf (DE)

(73) Assignee: Weber Maschinenbau GmbH Breidenbach, Breidenbach (DE)

( * ) Notice: Subject to any disclaimer, the term of this patent is extended or adjusted under 35 U.S.C. 154(b) by 43 days.

(21) Appl. No.: 16/434,695

(22) Filed: Jun. 7, 2019

(65) Prior Publication Data
US 2019/0376911 A1 Dec. 12, 2019

(30) Foreign Application Priority Data
Jun. 7, 2018 (DE) .................... DE102018113618.8

(51) Int. Cl.
| | | |
|---|---|---|
| *G01N 23/083* | (2018.01) | |
| *A23L 7/126* | (2016.01) | |
| *B65G 15/30* | (2006.01) | |
| *G01N 33/02* | (2006.01) | |
| *G01N 1/00* | (2006.01) | |

(52) U.S. Cl.
CPC ............ *G01N 23/083* (2013.01); *A23L 7/126* (2016.08); *B65G 15/30* (2013.01); *G01N 33/02* (2013.01); *G01N 2001/002* (2013.01)

(58) Field of Classification Search
None
See application file for complete search history.

(56) References Cited

U.S. PATENT DOCUMENTS

| | | | |
|---|---|---|---|
| 4,937,451 A | 6/1990 | Takada et al. | |
| 5,754,617 A | 5/1998 | Itoh | |
| 7,293,308 B2 * | 11/2007 | Everett | ................ A61B 5/0555 |
| | | | 5/601 |
| 9,869,642 B2 | 1/2018 | Dueppre | |
| 2012/0073415 A1 | 3/2012 | Maidel et al. | |

(Continued)

FOREIGN PATENT DOCUMENTS

| | | |
|---|---|---|
| DE | 32 46 568 A1 | 6/1984 |
| DE | 10 2012 018 754 A1 | 3/2014 |
| EP | 2 711 701 A1 | 3/2014 |

(Continued)

OTHER PUBLICATIONS

German Search Report dated Oct. 17, 2018, Application No. 10 2018 113 618.8, Applicant Weber Maschinenbau GmbH Breidenbach, 9 Pages.

(Continued)

*Primary Examiner* — Hoon K Song
(74) *Attorney, Agent, or Firm* — Fitch, Even, Tabin & Flannery LLP (57) ABSTRACT

The disclosure relates to a scanning apparatus for scanning food bars for a food processing system. The scanning apparatus comprises a conveyor assembly for conveying a food bar in a longitudinal direction, and a scanning unit adapted to record an outer and/or inner shape of at least one food bar. The scanning unit is movable at least along the longitudinal direction. The disclosure further relates to a method for scanning food bars.

21 Claims, 2 Drawing Sheets

(56) References Cited

U.S. PATENT DOCUMENTS

2014/0083268 A1* 3/2014 Rother ................. B26D 7/0625
                                                          83/52
2016/0128656 A1* 5/2016 Gregerson ........... A61B 6/4429
                                                          180/209

FOREIGN PATENT DOCUMENTS

| JP | 2008-209307 A | 9/2008 |
| WO | 2007/049305 A1 | 5/2007 |
| WO | 2010/112239 A2 | 10/2010 |

OTHER PUBLICATIONS

European Search Report and Opinion dated Oct. 16, 2019, Application No. 19178444.6-1022, Applicant Weber Maschinenbau GmbH Breidenbach, 10 pages.

* cited by examiner

APPARATUS AND METHOD FOR SCANNING FOOD BARS WITH MOVABLE SCANNING UNIT

CROSS-REFERENCE TO RELATED APPLICATIONS

This application claims foreign priority benefits under 35 U.S.C. § 119(a)-(d) to German patent application number DE 10 2018 113 618.8, filed Jun. 7, 2018, which is incorporated by reference in its entirety.

TECHNICAL FIELD

The present disclosure relates to a scanning apparatus for scanning food bars for a food processing system, comprising a conveyor assembly for conveying a food bar in a longitudinal direction, and a scanning unit adapted to record the outer and/or inner shape of at least one food bar. The present disclosure further relates to a method for scanning food bars, in which a food bar is conveyed in a longitudinal direction by way of a conveyor assembly, and the food bar is scanned by use of a scanning unit.

BACKGROUND

A food processing device is known in prior art from DE 10 2012 018 754 A1 and EP 2 711 701 A1 in which food products can be conveyed in succession through a scanning region of a scanner on separately drivable parallel conveying lanes.

Furthermore, it is known from WO 2007/049305 A1 to examine a piece of meat by way of an X-ray apparatus and a device for determining the thickness, and to quantify its properties.

Generic scanning apparatuses typically comprise a housing, in particular, for shielding X-ray radiation of the scanning unit, or for preventing that a light-based measurement is impaired in its measurement accuracy by ambient light.

The scanning devices known in prior art are often of a considerable length and therefore have a large housing, resulting in an increased installation effort and an extension of the line length of the food processing line.

SUMMARY

It is an object of the present disclosure to provide a scanning apparatus and a method for scanning food bars that allow for compact dimensions of the apparatus and efficient operation.

The present disclosure provides a scanning apparatus for scanning food bars for a food processing system, comprising a conveyor assembly for conveying a food bar in a longitudinal direction, and a scanning unit adapted to record the outer and/or inner shape of at least one food bar, where the scanning unit is movable according to the disclosure at least along the longitudinal direction. With the scanning unit being movable in the longitudinal direction, the food bar can be kept stationary during scanning, or, in addition to the motion of the scanning unit in the longitudinal direction, can be moved predominantly in the direction opposite to this movement. This reduces the space required for the food bar during the scanning process. Furthermore, the scanning efficiency can be increased if an acceleration of the scanning is enabled by combining the motion in opposite directions of the food bar and the scanning unit. The scanning process determines information about the outer and/or inner shape of the food bar by use of an imaging process. The food bars are aligned, in particular, in the conveying direction of the scanning apparatus, which then corresponds to the longitudinal direction.

The food processing system is preferably a system comprising a cutting machine which is downstream of the scanning apparatus and with which the scanned food bars can be sliced, where the scan result can be taken into account in controlling the slicing procedure in order to adjust the slice thicknesses and/or to perform a classification or grouping of the slices. Furthermore, a packaging machine can be provided downstream of the scanning apparatus. A central controller and/or a communication device, e.g., a bus system, can connect the aforementioned components of the food processing system to enable data exchange among the components.

The food bars are, in particular, elongated food products having a cross-section that is uniform or varies in the longitudinal direction, and which can be structured in a homogeneous or non-homogeneous manner. The food bars are, in particular, cheese sticks, sausage sticks, elongated loafs of ham as well as other food products of an elongated shape.

In particular, several elongated food bars can be lined up one behind the other in a conveyor lane and scanned together, for example, several short ham or cheese bars in an arrangement one behind the other. A scanning apparatus configured for longer food bars can then be used efficiently also for shorter food bars.

In one preferred embodiment, the scanning apparatus comprises a protective housing having an interior that is adapted to receive the at least one food bar during the scanning process, so that the latter can be arranged therein, where the length of the interior of the protective housing in the longitudinal direction is shorter than twice the length of a food bar. The food bar can then be disposed within the protective housing during the entire scanning process. Without the longitudinally movable scanning unit, however, a housing which has at least twice the length of the food bar is necessary in prior art, since the food bar must be completely moved through the scanning plane during the scanning process, so that it is previously arranged entirely in front of the scanning plane, and thereafter entirely behind the scanning plane. The length of a food bar is its maximum extension in the longitudinal direction, with or without considering end pieces that are reduced in diameter, in particular, are rounded. The food bars largely have a length between 15 cm and 180 cm, in particular, between 20 cm and 100 cm. In particular natural products have an irregular shape and/or structure and are advantageously measured on the feed side.

The scanning apparatus is set up such that the scanning unit is moved in an uninterrupted manner along the entire length of the food bar during scanning.

The protective housing advantageously comprises an inlet to be opened and closed and an outlet to be opened and closed. These are, in particular, openings in the protective housing which can be opened or closed by pivoting or sliding gates. The gates can be opened or closed advantageously by actuators that can be actuated by a central controller. Depending on the scanning technique, it can then be prevented that X-ray radiation escapes to the outside or that the scanning in the interior of the protective housing is negatively influenced by external factors, such as, for example, ambient light.

The food bars are advantageously accommodated entirely in the protective housing during the scanning process.

In one embodiment, the scanning unit comprises an X-ray device which is adapted to emit rays through the food bar. Information about the internal structure of the food bar can then be obtained, especially about the density distribution therein. For this purpose, a radiation source and a detector unit are arranged on opposite sides of the food bar.

The irradiation takes place, in particular, along a scanning plane or X-ray plane, the normal of which is oriented substantially in the direction of the longitudinal direction. The denser and higher the food bar is along a ray path, the more radiation is absorbed. The detector unit determines the intensity of the radiation, whereby conclusions about the density and/or height of the food bar are obtained by comparison with the energy of the radiation source or with reference measurements.

The detector unit can be configured, in particular, similar to a line scan camera which can respectively record the course of the absorption in the width direction of the food bar. When the scanning unit is moved, slice-by-slice measurements are conducted in the longitudinal direction of the food bar so that a density map can be calculated at the end in the longitudinal and the width direction of the entire food bar or at least for its region intended for slicing. Alternatively, a computer tomography X-ray device can be provided in the scanning unit and generate density maps in the height and width directions for every measurement, so that a 3D density map in the height, width and longitudinal directions can be calculated by moving the scanning unit in the longitudinal direction.

A geometry scanner can be provided alternatively or in addition to the x-ray device. The geometry scanner can determine the outer contour of the food bar at least in sections by way of an optical measuring method. The geometry scanner can be provided as part of the scanning unit and be movable in the longitudinal direction as part thereof. The geometry scanner can be disposed upstream of the X-ray device or even integrated directly thereinto.

Alternatively, however, the geometry scanner can also be provided stationary and, for example, scan the food bars when they move into the scanning apparatus, in particular into its protective housing. The geometry scanner comprises, in particular, a laser emitter which projects a line onto the food bar. The line projected thereonto is recorded by a camera which is arranged at a different angle than the laser emitter. The outer contour of the food bar can be calculated from the course of the line. If the food bar is moved through the geometry scanner or the geometry scanner is moved along the food bar, respectively, then the entire outer contour of the food bar can be determined. Consequently, the volume of the food bar is known.

The properties of the food bar determined by the geometry scanner can be used to control the x-ray device, in particular to regulate its performance as a function of the volume, with the aim of keeping the radiation exposure as low as possible.

The geometry scanner can be provided at any location in or on the protective housing. When recording the geometry above a (closed) support, the support area of the food bar can be co-determined by extrapolation.

Conventional X-ray methods, which are currently predominantly in X-ray devices for food bars, cannot distinguish between external geometric variation and internal geometric variations. Likewise, a variation in density cannot always be reliably distinguished from a variation in the composition of the food bar.

The additional recording of the volume of the food bar by way of a geometry scanner allows for a greater differentiation, since the entry point and exit point of the X-ray beam along an X-ray direction in the food bar can be determined.

The volume recorded by the geometry scanner and the data record acquired by the x-ray device can be evaluated jointly e.g., to compensate for the influence of the external geometry of the food bar on the absorption of the X-rays.

The geometrically recorded volume can be used to determine whether there are any external or internal variations in the food bars. An example of an internal variation is fermentation residue in a baked product, such as bread. An example of an external variation in shape is, for example, a fermentation crack in a baked product, for example in a bread surface.

The scan data recorded by the combination of the geometry scanner and the x-ray device provides more detailed information about the structure of the food bar and allows for improved further processing of the food bar. The slicing operation or cutting plan of a slicing machine can be directly influenced based on the scan data. For example, a defective region in the food bar can be marked as discard, and later discharged. Furthermore, a food bar can be sorted out from the process or specifically classified.

In one embodiment, the conveyor assembly comprises a circulating conveying device, and provided between the latter's upper support area and lower return area is a detector unit of the X-ray device. Alternatively, however, a radiation source can also be provided in that position, and the detector unit can be arranged above the food bar.

The circulating conveying device can be backed by a backing device to hold the food bar at a defined position, advantageously in a horizontal plane. The backing device is provided in particular directly beneath the conveying or upper run of the circulating conveying device.

In particular, a backing device in the form of a flat or concave plate-shaped lower support can be provided on which the conveying device runs, so that the conveying device and the food bar are backed and held in position in a defined manner. The backing device preferably has a uniform thickness, and extends end-to-end over the food bar length or the support area for the food bar.

For example, longitudinal struts can be provided as backing devices. In particular, two longitudinal struts can advantageously be arranged in the lateral edge region of the conveying device. This makes it possible to minimize interference with the scanning process performed by the scanning unit.

In one embodiment, it is possible that the backing device is movable together with the scanning unit. In particular, a recess can be provided in the backing device in the scanning plane. As a result, negative effects, in particular shielding effects, can be avoided during the scanning process.

The backing device is preferably made of material that absorbs little X-radiation.

If the position and in particular the material of the backing device is known or a reference image without the food bar has been created, then the interference influence of the backing device can be deducted from the data record determined by the scanning unit, so that a more accurate image solely of the food bar is created.

The reference image can be created in particular at regular intervals, for example, to compensate for contamination of the conveying device by adhesion of food ingredients, or to compensate for other conveyor belts, straps or chains, if used. In particular, the reference image can be newly created following the startup, after cleaning or after processing a food batch.

The circulating conveying device is advantageously at least one conveyor belt, at least one conveyor chain, or at least one conveyor strap.

In one embodiment, the conveyor assembly can comprise a circulating conveying device, where a belt gap defined by deflection rollers and movable in the longitudinal direction is provided in the upper support area of the conveyor assembly. The scanning unit is in particular aligned toward the belt gap and can be moved together therewith. Interference influence of the conveying device on the scanning process is then avoided. During the scanning process, the food bar extends over the belt gap and the latter can be moved along its longitudinal extension, advantageously while keeping the food bar substantially stationary. The conveyor assembly comprises, in particular, only one circulating conveying device. In other embodiments, it is also possible to provide several separate conveying devices, where the belt gap is provided, in particular, between circulating conveying devices, in particular conveyor belts, corresponding on the inlet side and on the outlet side.

In one embodiment, the conveyor assembly comprises two retraction belts, the deflection rollers of which being movable in the longitudinal direction define the edges of the belt gap. The configuration as two separate retraction belts makes it possible, in particular, that the conveying speeds can differ and the width of the belt gap can be flexibly adjusted. However, it is also possible to enable adjustment of the width of the belt gap in the longitudinal direction even with only one circulating conveying device in that a length compensation element is provided in the conveying device, for example, an adjustable deflection roller.

In particular the width of the belt gap can be reduced if the food bar is moved into the scanning apparatus prior to scanning. This enables reliable and fast conveying of the food bar. During the scanning process, the belt gap is then set to the necessary width to enable trouble-free scanning of the food bar.

The deflection rollers can be coupled mechanically or by control technology in the longitudinal direction in order to ensure a constant length of the belt gap. This coupling comprises, in particular, also the X-ray device or the scanning unit, respectively. The mechanical coupling can preferably be formed by a mechanical connecting element, for example, a connecting rod. The deflection rollers adjoining the belt gap can each be connected to the connecting element or mounted therein. In some embodiments, the scanning unit can be coupled to the belt gap mechanically or by control technology in the longitudinal direction at least temporarily, i.e., in particular during the scanning process, so that the scanning unit can be moved only together with the belt gap.

In one preferred embodiment, the conveyor assembly comprises several parallel conveying lanes. The throughput through the scanning apparatus can thus be increased. It is in particular possible for one food bar to be scanned in one of the parallel conveying lanes or for multiple food bars to be scanned in a subgroup of parallel conveying lanes while the food bars in other parallel conveying lanes are moved to the scanning position or are waiting in the scanning position.

In a multi-lane scanning apparatus, the scanning process can extend over at least two lanes. Image data evaluation is then used to assign the measured data to the respective lane and the food bar scanned there.

In a multi-lane scanning apparatus, a broad conveying device can be provided for several food bars with an end-to end belt gap. Otherwise, at least one separate conveying device can also be provided for every lane.

In one embodiment, the scanning unit is movable between the conveying lanes in the transverse direction. This enables food bars in multiple conveying lanes to be scanned sequentially with one scanning unit.

In one embodiment, a scanning unit movable in the longitudinal direction can be provided for every conveying lane or for every one subgroup of conveying lanes. The food bars can therewith be scanned simultaneously in each conveying lane or in each subgroup of the conveying lanes. In one embodiment, a common scanning unit is provided for all lanes. This allows all food bars in all lanes to be scanned simultaneously.

In one embodiment, the parallel conveying lanes are operable independently of each other. Consequently, the food bars in the individual lanes can be moved not only together, but alternatively sequentially individually or sequentially in groups through the scanning apparatus. This has the advantage that the scanning process can be made more flexible, food bars can in particular be conveyed in, scanned, and conveyed out on different lanes sequentially and/or independently. Consequently, the efficiency of the scanning apparatus can be increased, and with a reduction in the number of simultaneously scanned food bars, the necessary scanning performance of the scanning unit, in particular, the intensity of the emitted X-radiation, can be reduced.

A controller, which in particular comprises a microcontroller, is preferably provided, where a drive of the conveying device, a drive for the scanning unit, and optionally a drive for positioning the belt gap can be actuated by way of the controller. In particular the conveying speed of the conveying device can be set with the drive of the conveying device. In particular the travel motion of the scanning unit along the longitudinal direction can be controlled with the drive of the scanning unit. Preferably the deflection rollers adjoining the belt gap or defining the belt gap, respectively, can be moved together or individually in the longitudinal direction with the drive for positioning the belt gap. Furthermore, compensation elements, which ensure that the predetermined tension of the conveyor belt is maintained despite the movement of the deflection rollers, can optionally be moved. Moving the compensation elements can be effected by the drive for positioning the belt gap, or by a separate drive.

The disclosure further provides a method for scanning food bars, comprising conveying a food bar in a longitudinal direction using a conveyor assembly and scanning the food bar using a scanning unit, where the scanning unit is moved according to the disclosure along the food bar in the longitudinal direction during scanning.

The scanning unit is advantageously moved in an uninterrupted manner along the entire length of the food bar during scanning.

Conveying the food bar can be interrupted during scanning. Consequently, the food bar can remain stationary while the scanning unit is being moved along the food bar. This allows for a compact configuration of the conveyor assembly and the scanning unit.

Conveying the food bar can be interrupted during the entire scanning process so that the food bar is stationary during the entire scanning process while the scanning unit is being moved. Alternatively, the food bar can be moved at least temporarily or even the entire time during scanning, in particular in the conveying or longitudinal direction and relative to the moving scanning unit. However, the food bar is moved only over a limited distance, which is determined in particular by the size of the protective housing.

In one embodiment, conveying the food bar can comprise moving the food bar into a protective housing, where the scanning unit is moved only within the protective housing. Consequently, it is possible to shield the scanning process from external influences and/or to prevent X-radiation from exiting from the protective housing.

In particular with optical scanning methods, the method can also be performed without a closed protective housing. Scanning can then also be performed when the food bar is moved in and/or out.

In one embodiment, the food bars are conveyed in several parallel lanes, where the scanning unit is moved in the transverse direction between the lanes to perform the scanning process in different lanes. Sequential scanning in multiple parallel lanes or subgroups of lanes can thereby be enabled with one scanning unit configured only for scanning in the width of a lane or a subgroup of lanes.

The scanning unit is advantageously moved in respective opposite directions for successive scanning processes. The scanning unit is moved, in particular, alternately in the conveying direction and in the direction opposite to the conveying direction. Therebetween, the scanning unit is advantageously moved in the transverse direction between the lanes. This allows several scanning processes to quickly follow one another since no return of the scanning unit to the starting position is necessary.

In one embodiment, the food bar is irradiated during scanning, and the result of the scanning process is corrected using reference data obtained during a scanning process without food bars. In particular, this reference data contains information regarding the components of the conveyor assembly arranged in the scanning plane which are irradiated together with the food bar. The conveyor assembly can comprise in particular components in the form of conveying devices, such as belts, straps or chains, or backing devices, such as backing plates or bars, which are irradiated together with the food bar. The effect of the irradiated components on the scan data is recorded as part of the reference data acquisition, so that correction of the scanned data of the food bar can take place in subsequent scan processes.

In one embodiment, the scanning unit is moved during scanning together with a belt gap of the conveyor assembly so that the scanning plane is always disposed within the belt gap during scanning. When using an X-ray device, it can then be prevented that the food bar is irradiated together with the conveyor assembly. Instead, only the food bar is irradiated, so that the conveyor assembly does not affect the measurement result. With a corresponding use of a geometry scanner, the food bar can be recorded from all sides.

During scanning and the corresponding displacement of the belt gap, the food bar is preferably kept stationary, namely by a correspondingly coordinated drive of the conveyor assembly.

Outside the scanning process, however, it is also possible that the food bar is moved at a different speed than the scanning unit or the belt gap, respectively. The speed of the food bar is determined by the drive of the conveyor assembly, the speed of the scanning unit by the speed of the belt gap positioning drive or by the drive of the scanning unit along the longitudinal direction, respectively. The scanning unit and the belt gap can therewith be moved back to a starting position or in any predeterminable initial position depending on the food bar, while the food bar of the scanning apparatus is conveyed in or out.

An exemplary sequence of the method according to the disclosure can be summarized as follows:

First, a food bar is moved into the protective housing by driving a respective conveying device. The scanning unit is arranged on a portal movable in the longitudinal direction and in the transverse direction. The portal moves the scanning unit to a downstream end region of a first conveying lane. The portal then moves the scanning unit fully over the entire food bar in a direction opposite to the longitudinal direction, so that the food bar is entirely scanned. The scanning unit is now at the upstream end region and is moved by way of the portal transversely to the parallel lane. The portal then moves the scanning unit in the conveying direction over the food bar arranged on the second lane, so that this food bar as well is entirely scanned. The food bars are then moved together out of the protective housing.

In one alternative embodiment, the scanning unit can be configured such that several conveying lanes can be scanned in parallel at the same time. In this alternative, several, in particular, lane-specific scanning units can be provided which can be moved either together with a portal or with separate holders individually per lane in the longitudinal direction.

The direction of motion of the scanning unit during scanning along the longitudinal direction is arbitrary, i.e., scanning can take place in particular in the upstream as well as in the downstream direction. Advantageously, the scanning unit is moved in respective opposite directions for successive scanning processes, so that return operations of the scanning unit can be avoided.

Example embodiments according to the present disclosure shall now be described with reference to the accompanying drawings.

DETAILED DESCRIPTION

Figure 1:
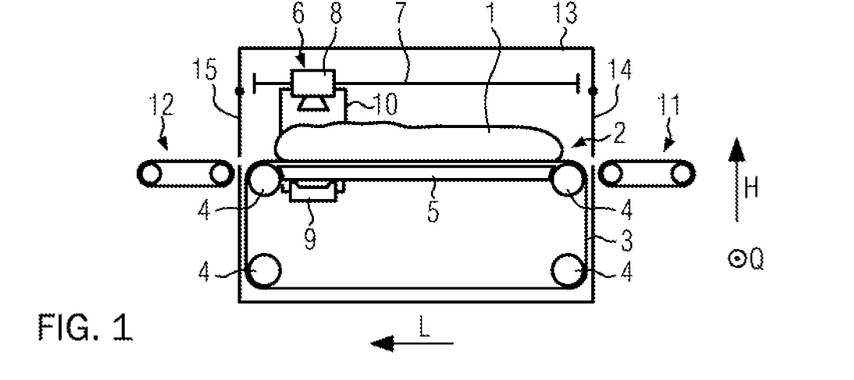
FIG. 1 shows a schematic side view of a first embodiment of a scanning apparatus according to the disclosure.

FIG. 1 shows a scanning apparatus and a food bar 1 arranged therein in a side view. The scanning apparatus comprises a conveyor assembly 2 which comprises a conveying device 3 in the form of a conveyor belt circulating around several deflection rollers 4. Conveyor assembly 2 further comprises a backing device 5, in particular in the form of a lower support, which is formed by a plate. Alternatively, one, two or more backing rods can be provided as backing device 5. Backing device 5 is located directly beneath the conveying device in its conveying region, and ensures that the conveying device is held in a predetermined position, even if a food bar 1 having more weight is arranged thereon. Furthermore, conveyor assembly 2 comprises a drive for conveying device 3 which controls the circulation of conveying device 3 around deflection rollers 4, and thereby conveys the food bar in the conveying direction or longitudinal direction L, respectively.

Furthermore, a scanning unit 6 is provided movable at least along longitudinal direction L. The longitudinal direction advantageously extends in the horizontal direction. The scanning plane has a normal in the longitudinal direction, therefore extends in vertical direction H and transverse direction Q.

Scanning unit 6 is slidable along a suspension or rail 7 in longitudinal direction L. The motion of scanning unit 6 is predetermined by a drive, which can be, in particular, a linear drive, for example a magnetic linear drive, but also a chain drive, a hydraulic or pneumatic drive or the like Scanning unit 6 comprises a radiation source 8 which comprises, in particular, an X-ray tube, and a detector unit 9. Detector unit 9 is, in particular, a line camera extending in transverse direction Q which can digitally record the intensity of the X-radiation in the scanning plane.

Scanning unit 6 is installed such that movability is given over the entire support area of food bar 1. In particular axial movability relative to longitudinal direction L of food bar 1 is given, so that X-ray scanning can take place when the food bar passes.

Alternatively, the scanning unit can be configured as a geometry scanner. The radiation source is then a light emitter, in particular a laser emitter, and the detector unit is an optical camera. However, the radiation source and the detector unit are then not arranged opposite to each other as shown, but at an angle smaller than 180°, since the reflection from the food bar and not its irradiation is then measured. In one embodiment, the scanning unit can comprise both an x-ray device as well as a geometry scanner.

Radiation source 8 and detector unit 9 are advantageously connected via a mechanical coupling 10 in the form of a frame or a coupling rod, so that they can be moved together. In other embodiments, however, it is also possible that the control unit and the detector unit are provided in separate guides and are movable individually, and are only moved synchronously for the scanning process, i.e., are coupled by control technology.

Radiation source 8 is preferably located above the support plane and detector unit 9 is located beneath the upper support run of conveying device 3. Radiation source 8 and detector unit 9 constitute an integrally formed X-ray device with fixedly assigned components.

FIG. 1 illustrates scanning unit 6 at a position near its most downstream position and, starting out from there, is moved during the scanning process along longitudinal direction L of food bar 1, namely in a direction opposite to longitudinal direction L. In a subsequent scanning process, scanning unit 6 can then be moved in longitudinal direction L of food bar 1.

As a result of the motion of scanning unit 6 along food bar 1, entire food bar 1 can be recorded by measurement technology with a scan slice by slice or in a discrete or continuous manner in the scanning plane that is moved along the food bar.

A density map of entire food bar 1 can be determined from the radiation passing through food bar 1. For this purpose, scanning unit 6 is moved from the downstream end to the upstream end of food bar 1 or, alternatively, from its upstream end to its downstream end.

In particular, a feed conveyor assembly 11 is provided with which food bar 1 can be fed to the scanning apparatus. Furthermore, a discharge conveyor assembly 12 is provided with which food bar 1 can be further conveyed starting out from the scanning apparatus. Feed conveyor assembly 11 and discharge conveyor assembly 12 can be, in particular, components of upstream or downstream stations. For example, discharge conveyor assembly 12 can be part of a loading conveyor assembly of a food slicing machine. The data determined by the scanning apparatus can be taken into account for controlling the food slicing machine.

The scanning apparatus comprises a protective housing 13 which has an entrance gate 14 and an exit gate 15. Gates 14, 15 are, in particular, hinged or sliding gates, which are provided with a drive to be opened or closed. Entrance gate 14 can be opened to move a food bar into the scanning apparatus. The gates are kept closed during the scanning process. Upon completion of the scanning process, exit gate 15 is opened to move the food bar out of the scanning apparatus.

In particular, scanning takes place in at least one lane, but scanning can also take place in parallel or sequentially in several parallel lanes.

One embodiment of a method according to the disclosure with the scanning apparatus according to FIG. 1 is as follows. Starting out from a feed conveyor assembly 11, food bar 1 is moved by conveyor assembly 2 through gate 14 into protective housing 13 of the scanning apparatus, and the gate is closed.

Scanning unit 6 is then moved in longitudinal direction L to scan the entire food bar while gates 14, 15 are closed. The food bar does not move during scanning. The scan data is then corrected on the basis of a reference image or by correction values with respect to the conveyor assembly.

The food bar is then moved out of protective housing 13 by way of conveyor assembly 2 through gate 15 onto discharge conveying device 12.

Figure 2:
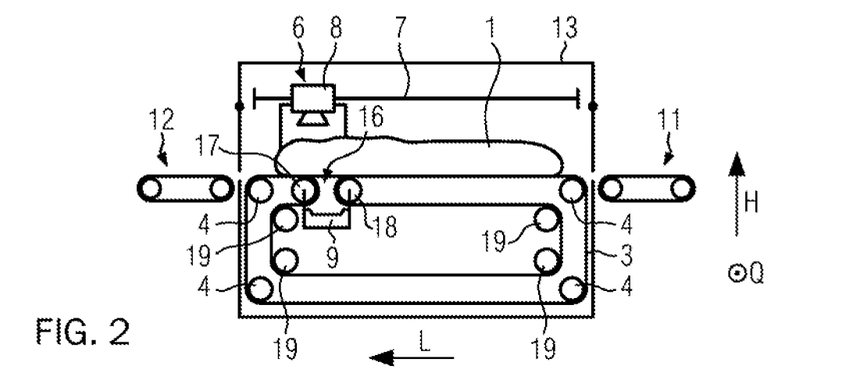
FIG. 2 shows a schematic side view of a second embodiment of a scanning apparatus according to the disclosure.

FIG. 2 shows a further embodiment of the scanning apparatus according to the disclosure. In this embodiment, conveyor assembly 2 comprises a belt gap 16 which is defined by two spaced deflection rollers 17, 18 of conveyor assembly 2. As shown in FIG. 2, the deflection rollers are mechanically coupled to each other in longitudinal direction L, so that a predetermined distance between them is maintained and the width of belt gap 16 is thus predetermined.

Conveying device 3 not only runs around outer deflection rollers 4 but also around inner deflection rollers 19. Consequently, it is possible that a belt gap exists despite only one integral circulating conveying device 3 being used. In the embodiment shown in FIG. 2, the width of the belt gap is uniform. Optionally, an adjustable compensation roller, not shown, can be provided and can be moved in particular translationally to adjust the width of the belt gap.

In the embodiment according to FIG. 2, radiation source 8 of scanning unit 6 is not mechanically coupled to detector unit 9, but is only moved in synchronism therewith, i.e., is coupled by control technology. Alternatively, however, a mechanical coupling is also possible.

In an alternative embodiment, a further belt gap can be provided in the lower run of conveyor assembly 2. This allows conveyor assembly 2 to be composed of two independently driven conveying devices, and the speed of moving in and moving out to be configured to differ, or conveying the food bar can be influenced flexibly in another manner. The conveying devices are then coupled to one another mechanically or by control technology and/or with regard to the belt gap motion. As a result, it can be ensured, in particular, that the relative arrangement of the belt gap and the two conveying devices relative to the scanning plane always remains the same.

Depending on the position of the food bar and the belt gap, the former is located more or less on the two conveying devices or conveying device sections upstream and downstream of the belt gap. In particular, the scanning plane can be moved by a coordinated motion of the belt gap and the conveying device(s) relative to the food bar. When the food bar is moved in or out, the belt gap is traversed by appropriately driving the conveying device(s) with the food bar. The belt gap can then, in particular, stand still.

However, it is also possible to move the belt when the product is moved in and out, either as part of a scanning process or for arranging the scanning unit at a starting position. When the food bar is moved in, the conveying device takes the food bar into position, i.e., places it in a suitable manner in the protective housing. The scanning unit and the belt gap can there be moved to the starting position for the next scanning process before or at the time when the food bar is moved in. Advantageously, the belt gap and the scanning unit are there positioned in an end region at one of the end sides of the protective housing in the longitudinal direction. Once the scanning unit has been moved to the starting position for the scanning process, only the conveying device(s) is/are driven to arrange the food bar fully in the housing if the food bar has not yet been not properly positioned. The gates of the protective housing are then closed and the scanning process is performed. A food bar can be moved into the protective housing while another food bar is moved out of the protective housing in the same lane, in particular, simultaneously. Advantageously, only a small spacing is maintained in the longitudinal direction between the food bars.

After the scanning process, the belt gap is disposed in the opposite end region relative to its initial starting position. The subsequent scanning process can then advantageously take place in the reverse direction of motion for the scanning unit. Alternatively, the belt gap or the scanning unit, respectively, can again be moved back to the starting position for the next pass before or at the time when the food bars are moved out of the scanning apparatus.

Figure 3:
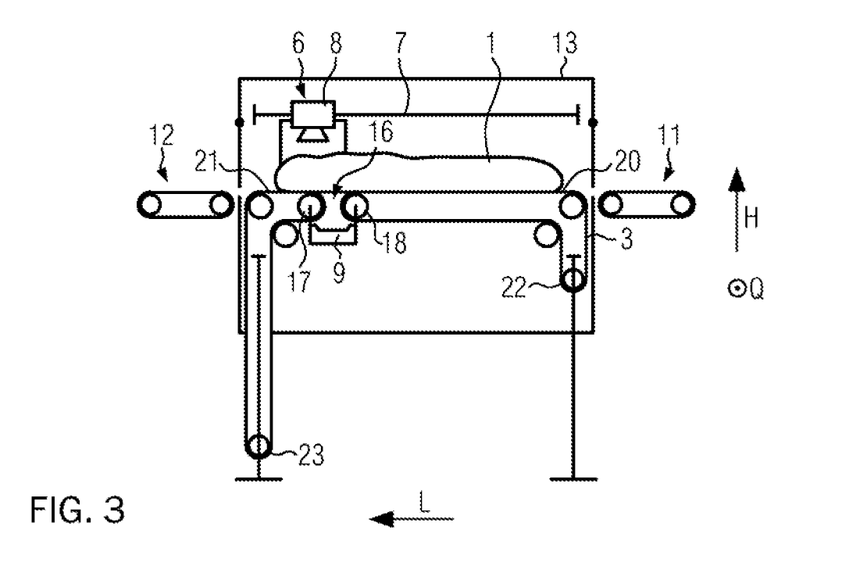
FIG. 3 shows a schematic side view of a third embodiment of a scanning apparatus according to the disclosure.

FIG. 3 shows a further embodiment of the scanning apparatus according to the disclosure. Conveyor assembly 3 there comprises a first conveying device 20 and a second conveying device 21. First conveying device 20 is arranged upstream of second conveying device 21, and a belt gap 16 is formed between conveying devices 20, 21. A detector unit 9 is arranged beneath belt gap 16. Conveying devices 20, 21 each comprise deflection rollers 17, 18 at their ends that are assigned to belt gap 16. Furthermore, conveying devices 20, 21 each comprise compensation rollers 22, 23 which can be moved along a guide, presently in particular along a vertical linear guide, in order to enable moving belt gap 16 in longitudinal direction L. Due to separate compensation rollers 22, 23, however, the width of belt gap 16 in the longitudinal direction L can also be readily adapted.

The belt gap can be almost completely closed while food bar 1 is moved into or out of the scanning apparatus. For this purpose, deflection rollers 17, 18, and therefore the belt ends, are moved closer to each other. This has the particular advantage that passing over of the belt gap or the belt transition is gentler to the food bar, whereby the detection unit located beneath the belt gap can be protected against contamination.

During the scanning process, the belt gap can then be moved to a distance in the longitudinal direction, so that the rays can pass from radiation source 8 to detector unit 9 without being impaired by the conveying device.

Conveying devices 20, 21 are formed as two separate retraction belts and coupled advantageously by control technology, but optionally additionally or alternatively mechanically to each other. A mechanical coupling is advantageously provided in the region of belt gap 16 and optionally couples the belt gap to scanning unit 6. The relative arrangement of belt gap 16 and the two conveying devices 20, 21 is then always the same, at least in the longitudinal direction.

Compensation rollers 22, 23 can be arranged independently in the enclosing protective housing 13 or extend out from the latter. The food bars are more or less disposed on the two conveying devices 20, 21 during the scanning process or during the process of being moved in or out.

Positioning the food bar with respect to the X-ray plane is effected by coordinated conveying device speeds of the two conveying devices 20, 21, as well as a coordinated belt retraction by moving compensation rollers 22, 23. In particular a controller which determines the conveying device speed and the movements of compensation rollers 22, 23 is provided so that no slippage occurs at the food bar.

FIGS. 4A to 4D each show a top view onto a further embodiment of a scanning apparatus according to the disclosure at different points in time of the operation.

The scanning apparatus comprises a conveyor assembly 2 with two parallel conveying devices 24 and 25, where a first belt gap 26 is provided in first conveying device 24 and a second belt gap 27 in second conveying device 25. The configuration of the conveying devices with respect to belt gaps 26, 27 can be effected according to FIG. 2 or 3.

Figure 4A:
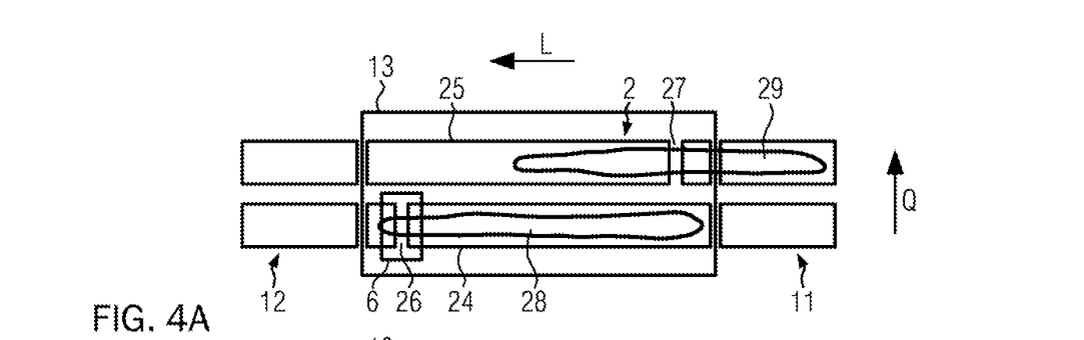
FIGS. 4A to 4D show a top view onto a fourth embodiment of a scanning apparatus according to the disclosure and illustrate the sequence of an embodiment of a method according to the disclosure.

A scanning apparatus 6 and belt gap 26 of first conveying device 24 are first moved to the starting position of the scanning with respect to first food bar 28 as shown in FIG. 4A. At the same time, a second food bar 29 is moved by feed conveyor assembly 11 on second conveying device 25 into protective housing 13.

Figure 4B:
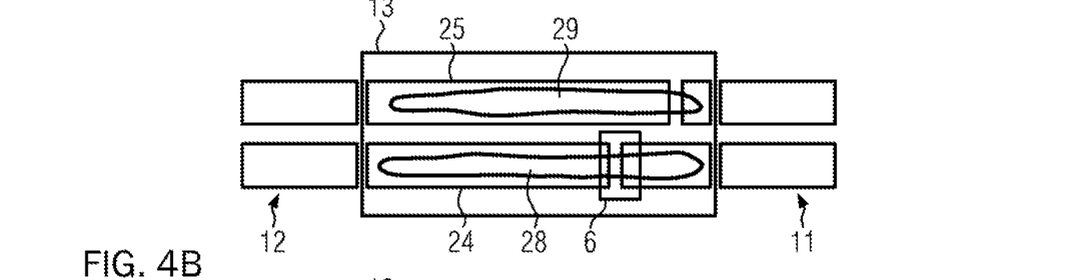
Figure 4C:
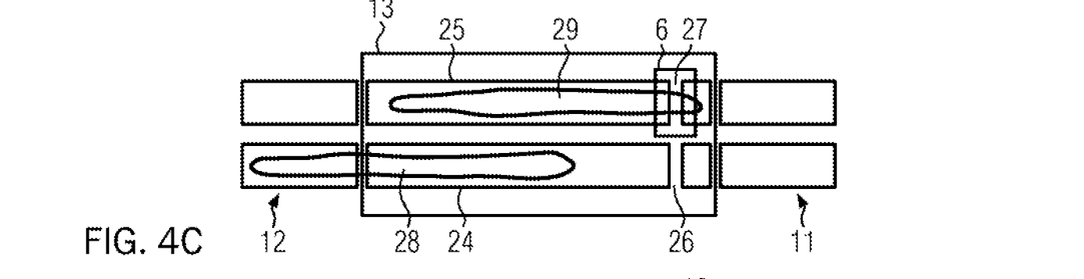

As shown in FIG. 4B, entire first food bar 28 is scanned by moving scanning unit 6 in a direction opposite to longitudinal direction L. First food bar 28 is arranged stationarily within protective housing 13. After the scanning process of first food bar 28 is completed, the scanning unit is moved in transverse direction Q toward second conveying device 25, so that scanning unit 6 is aligned with the former's belt gap 27, as shown in FIG. 4C. By moving scanning unit 6 and belt gap 27 in longitudinal direction L, second food bar 29 is then scanned along its entire length.

Figure 4D:
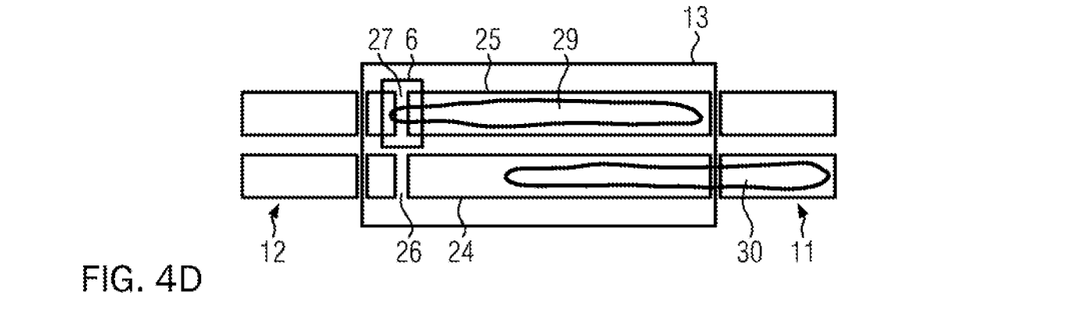

As can be seen in FIG. 4D in comparison to FIG. 4C, during or after scanning food bar 29 on second conveying device 25, belt gap 27 of first conveying device 24 is moved in longitudinal direction L back to its starting position, as shown in FIGS. 4D and 4A.

After scanning of second food bar 29 has been completed, a third food bar 30 is moved in onto first conveying device 24. Scanning unit 6 is then again moved transversely, so that food bar 30 on first conveying device 24 can then be scanned.

Scanning device 6 can in particular be attached to a portal and can be moved along this portal longitudinally and transversely between the conveying lanes.

The aforementioned embodiment with two parallel belts can also be embodied without a belt gap, for example, with a configuration according to FIG. 1, where the measured scan image should then optionally be corrected by way of a reference image of the product support.

The disclosure enables the protective housing of the scanning unit to be only about as long as the longest food bar to be scanned. This results in a shortened line length and easier integration of the scanning apparatus or a simpler installation in a production operation, respectively. In addition, the construction complexity is reduced. Furthermore, a time advantage in the scanning process is enabled because no return action is necessary, and a smooth entry and exit of food bars is possible. A combination of an X-ray scanner and a geometry scanner in the scanning unit results in a modular scanning apparatus which can then also be easily retrofitted depending on the application.

In alternative embodiments, the detector unit can be arranged above the food bar and the scanning unit therebeneath. In other embodiments, it is possible to arrange the scanning unit on one side in the transverse direction adjacent to the food bar and the detector unit on the opposite side.

What is claimed is:

1. A scanning apparatus for scanning food bars for a food processing system, the scanning apparatus comprising:
    a conveyor assembly for conveying a food bar in a longitudinal direction; and
    a scanning unit which is adapted to record an outer shape and/or inner shape of the food bar;
    wherein the scanning unit is movable at least along the longitudinal direction; and
    a protective housing with an interior in which the food bar is arrangeable during the scanning process, wherein a length of the interior of the protective housing in the longitudinal direction is shorter than twice a length of the food bar.

2. The scanning apparatus according to claim 1, wherein the scanning unit comprises a radiation source which is adapted to irradiate the food bar.

3. The scanning apparatus according to claim 1, wherein the conveyor assembly comprises a circulating conveying device having an upper support area and a lower return area, and the scanning unit comprises a detector unit provided between the upper support area and the lower return area.

4. The scanning apparatus according to claim 1, wherein the conveyor assembly comprises a circulating conveying device, and wherein a belt gap defined by deflection rollers and movable in the longitudinal direction is provided in an upper support area of the conveyor assembly.

5. The scanning apparatus according to claim 4, wherein the deflection rollers are mechanically coupled in the longitudinal direction by a coupling to ensure a constant length of the belt gap, and wherein the coupling comprises the scanning unit.

6. The scanning apparatus according to claim 1, wherein the conveyor assembly comprises two conveying devices that each include a retraction belt and a deflection roller, and wherein the deflection rollers are movable in the longitudinal direction and define a belt gap that is movable in the longitudinal direction.

7. The scanning apparatus according to claim 1, wherein the conveyor assembly comprises a plurality of parallel conveying lanes.

8. The scanning apparatus according to claim 7, wherein the scanning unit is movable between the plurality of parallel conveying lanes in a transverse direction.

9. The scanning apparatus according to claim 7, wherein a scanning unit movable in the longitudinal direction is provided for each of the plurality of parallel conveying lanes or for each of a plurality of subgroups of the plurality of parallel conveying lanes.

10. The scanning apparatus according to claim 7, wherein the plurality of parallel conveying lanes are operable independently of each other.

11. The scanning apparatus according to claim 1, further comprising a controller configured to actuate a drive for the conveyor assembly, a drive for the scanning unit, or a drive for positioning the belt gap.

12. A method for scanning food bars, the method comprising:
    conveying a food bar in a longitudinal direction using a conveyor assembly;
    scanning the food bar using a scanning unit; and
    moving the scanning unit along the food bar in the longitudinal direction during the scanning;
    wherein conveying the food bar comprises moving the food bar into a protective housing, and wherein the scanning unit is moved only within the protective housing.

13. The method according to claim 12, wherein the scanning unit is moved along an entire length of the food bar during the scanning.

14. The method according to claim 12, wherein conveying the food bar is interrupted during the scanning.

15. The method according to claim 12, wherein food bars are conveyed in multiple parallel lanes, and wherein the scanning unit is operated to scan the food bars and is moved between the lanes in a transverse direction in-between scanning processes.

16. The method according to claim 12, wherein the scanning unit is moved in respective opposite directions for successive scanning processes.

17. The method according to claim 12, wherein the food bar is irradiated during scanning, and a result of the scanning is corrected using reference data determined in a scanning process without the food bar.

18. The method according to claim 12, wherein the scanning unit during scanning is moved together with a belt gap of the conveyor assembly, and scanning is performed within the belt gap.

19. A scanning apparatus for scanning food bars for a food processing system, the scanning apparatus comprising:
    a conveyor assembly for conveying a food bar in a longitudinal direction; and
    a scanning unit which is adapted to record an outer shape and/or inner shape of the food bar;
    wherein the scanning unit is movable at least along the longitudinal direction, and the conveyor assembly comprises a circulating conveying device, wherein a belt gap defined by deflection rollers and movable in the longitudinal direction is provided in an upper support area of the conveyor assembly.

20. A scanning apparatus for scanning food bars for a food processing system, the scanning apparatus comprising:
    a conveyor assembly for conveying a food bar in a longitudinal direction; and
    a scanning unit which is adapted to record an outer shape and/or inner shape of the food bar;
    wherein the scanning unit is movable at least along the longitudinal direction;
    wherein the conveyor assembly comprises two conveying devices that each include a retraction belt and a deflection roller, and wherein the deflection rollers are movable in the longitudinal direction and define a belt gap that is movable in the longitudinal direction.

21. A method for scanning food bars, the method comprising:
    conveying a food bar in a longitudinal direction using a conveyor assembly;
    scanning the food bar using a scanning unit; and
    moving the scanning unit along the food bar in the longitudinal direction during the scanning;
    wherein the scanning unit during scanning is moved together with a belt gap of the conveyor assembly, and scanning is performed within the belt gap.

* * * * *